United States Patent
Gatzemeyer et al.

(10) Patent No.: US 8,517,728 B2
(45) Date of Patent: Aug. 27, 2013

(54) ORAL CARE IMPLEMENT HAVING FLUID DELIVERY SYSTEM

(75) Inventors: John J. Gatzemeyer, Hillsborough, NJ (US); Thomas J. Boyd, Metuchen, NJ (US); Eduardo J. Jimenez, Manalapan, NJ (US); Bruce M. Russell, Howell, NJ (US)

(73) Assignee: Colgate-Palmolive Company, New York, NY (US)

( * ) Notice: Subject to any disclaimer, the term of this patent is extended or adjusted under 35 U.S.C. 154(b) by 0 days.

(21) Appl. No.: 11/626,617

(22) Filed: Jan. 24, 2007

(65) Prior Publication Data

US 2008/0176183 A1    Jul. 24, 2008

(51) Int. Cl.
*A46B 11/04*    (2006.01)

(52) U.S. Cl.
USPC ............... 433/80; 433/89; 433/216; 401/270; 401/282

(58) Field of Classification Search
USPC ........ 433/80, 82, 83, 88, 215, 216; 15/167.1, 15/22.1, 22.2; 132/308, 309, 311, 322; 118/200; 401/270, 282, 283, 291
See application file for complete search history.

(56) References Cited

U.S. PATENT DOCUMENTS

| | | | |
|---|---|---|---|
| 1,798,081 A | 3/1931 | Gordyn, Jr. et al. | |
| 1,973,212 A | 9/1934 | Krueger | |
| 2,416,684 A | 3/1947 | Fischer | |
| 2,573,201 A | 10/1951 | Kelley et al. | |
| 2,594,721 A | 4/1952 | Beebe | |
| 2,739,328 A | 3/1956 | Bemier | |
| 3,369,543 A | 2/1968 | Ronco | |
| 3,685,080 A | 8/1972 | Hubner | |
| 3,810,479 A | 5/1974 | Miles | |
| 3,902,510 A | 9/1975 | Roth | |
| 3,910,706 A * | 10/1975 | Del Bon | 401/134 |
| 3,936,200 A | 2/1976 | O'Rourke | |
| 3,937,582 A | 2/1976 | Del Bon | |
| 4,023,580 A | 5/1977 | Pieters | |
| 4,060,870 A | 12/1977 | Cannarella | |
| 4,088,412 A | 5/1978 | Del Bon | |
| 4,124,316 A | 11/1978 | O'Rourke | |
| 4,236,651 A | 12/1980 | Meyer et al. | |

(Continued)

FOREIGN PATENT DOCUMENTS

| | | |
|---|---|---|
| CN | 2343878 | 10/1999 |
| DE | 3113450 | 10/1982 |

(Continued)

OTHER PUBLICATIONS

International Search Report Dated Aug. 4, 2008.

(Continued)

*Primary Examiner* — Yogesh Patel

(57) ABSTRACT

An oral care implement has a head portion with tooth cleaning elements on one surface thereof and a reservoir containing at least one active agent. A capillary channel extends through at least a portion of the oral care implement to deliver active agent(s) to one or more outlets. In one aspect, a vibration-producing device is provided to vibrate at least a portion of the implement to enhance the function of tooth cleaning elements and the delivery of the active agent through capillary action. A variety of active agents can be administered for therapeutic, hygienic, and/or other benefits, such as fresh breath, tooth whitening, or producing sensations of heat, cool, or tingling.

17 Claims, 7 Drawing Sheets

(56) References Cited

U.S. PATENT DOCUMENTS

| | | | |
|---|---|---|---|
| 4,304,245 A | 12/1981 | Lichfield | |
| 4,462,136 A | 7/1984 | Nakao et al. | |
| 4,509,541 A | 4/1985 | Manciocchi, Jr. | |
| 4,521,128 A | 6/1985 | O'Neal | |
| 4,538,631 A | 9/1985 | Prince | |
| 4,543,679 A * | 10/1985 | Rosofsky et al. | 15/110 |
| 4,585,018 A | 4/1986 | O'Connor | |
| 4,716,035 A | 12/1987 | Sampathkumar | |
| 4,733,586 A | 3/1988 | Manusch et al. | |
| 4,753,249 A | 6/1988 | Muller | |
| 4,828,420 A | 5/1989 | Otsuka et al. | |
| 4,867,183 A | 9/1989 | Busch et al. | |
| 2,154,209 A | 8/1990 | Kohn | |
| 4,973,181 A | 11/1990 | Jankewitz | |
| 4,990,329 A | 2/1991 | Sampathkumar | |
| 5,000,193 A | 3/1991 | Heelis et al. | |
| 5,017,036 A | 5/1991 | Vidovic | |
| 5,033,898 A * | 7/1991 | Williams | 401/283 |
| 5,062,728 A * | 11/1991 | Kuo | 401/176 |
| 5,066,155 A | 11/1991 | English et al. | |
| 5,088,627 A | 2/1992 | Musel | |
| 5,094,254 A | 3/1992 | Krueckel et al. | |
| 5,096,319 A * | 3/1992 | Gueret | 401/126 |
| 5,098,297 A | 3/1992 | Chari et al. | |
| 5,102,251 A | 4/1992 | Kaufmann | |
| D337,659 S * | 7/1993 | Lacy | D4/116 |
| 5,309,590 A | 5/1994 | Giuliani et al. | |
| 5,346,324 A | 9/1994 | Kuo | |
| 5,352,052 A | 10/1994 | Kaufmann | |
| 5,407,287 A | 4/1995 | Braun et al. | |
| 5,458,563 A | 10/1995 | Stewart | |
| 5,463,792 A | 11/1995 | Hogan et al. | |
| 5,476,384 A * | 12/1995 | Giuliani et al. | 433/216 |
| 5,490,529 A | 2/1996 | Fitjer | |
| 5,490,736 A | 2/1996 | Haber et al. | |
| 5,492,426 A | 2/1996 | Gueret | |
| 5,509,742 A | 4/1996 | Balzarini | |
| 5,578,023 A | 11/1996 | Schneider | |
| 5,611,687 A * | 3/1997 | Wagner | 433/80 |
| 5,769,553 A | 6/1998 | Chaudhri et al. | |
| 5,829,976 A | 11/1998 | Green | |
| 5,842,248 A | 12/1998 | van Grol et al. | |
| 5,865,195 A * | 2/1999 | Carter | 132/309 |
| 5,875,798 A | 3/1999 | Petrus | |
| 5,910,122 A | 6/1999 | D'Angelo | |
| 6,039,489 A | 3/2000 | Harman et al. | |
| 6,082,999 A | 7/2000 | Tcherny et al. | |
| 6,089,776 A | 7/2000 | Kaufmann | |
| 6,095,707 A | 8/2000 | Kaufmann | |
| 6,142,694 A | 11/2000 | Rivlin et al. | |
| 6,164,858 A | 12/2000 | Kaufmann | |
| 6,183,155 B1 | 2/2001 | Kaufmann | |
| 6,203,320 B1 | 3/2001 | Williams et al. | |
| 6,205,611 B1 * | 3/2001 | Vigil | 15/244.1 |
| 6,206,600 B1 | 3/2001 | Rosenberg et al. | |
| 6,244,774 B1 | 6/2001 | Barosso et al. | |
| 6,244,777 B1 | 6/2001 | Reid | |
| 6,322,268 B1 | 11/2001 | Kaufmann et al. | |
| 6,345,405 B1 * | 2/2002 | Brackin | 15/106 |
| 6,371,674 B1 * | 4/2002 | Lerner | 401/155 |
| 6,378,529 B1 | 4/2002 | Clemente Marco | |
| 6,418,940 B1 | 7/2002 | Tcherny et al. | |
| 6,434,773 B1 | 8/2002 | Kuo | |
| D465,625 S | 11/2002 | Price | |
| 6,497,527 B2 | 12/2002 | Kaufmann | |
| 6,533,734 B1 | 3/2003 | Corley, III et al. | |
| RE38,150 E | 6/2003 | Greatbatch et al. | |
| 6,599,048 B2 | 7/2003 | Kuo | |
| 6,623,698 B2 | 9/2003 | Kuo | |
| 6,663,679 B1 | 12/2003 | Duncan | |
| 6,669,390 B1 | 12/2003 | Porter et al. | |
| 6,669,475 B2 | 12/2003 | Kandelman et al. | |
| 6,669,930 B1 | 12/2003 | Hoic et al. | |
| 6,770,266 B2 | 8/2004 | Santarpia, III et al. | |
| 6,802,097 B2 | 10/2004 | Hafliger et al. | |
| 6,817,803 B1 | 11/2004 | Ong et al. | |
| 6,895,629 B1 | 5/2005 | Wenzler | |
| 6,899,280 B2 | 5/2005 | Kotary et al. | |
| 6,902,337 B1 | 6/2005 | Kuo | |
| 6,932,603 B2 | 8/2005 | Han et al. | |
| 6,932,604 B2 | 8/2005 | Han et al. | |
| D510,482 S | 10/2005 | Jimenez | |
| 7,003,839 B2 | 2/2006 | Hafliger et al. | |
| 7,021,851 B1 | 4/2006 | King | |
| 7,025,521 B2 | 4/2006 | Tsaur | |
| 7,108,868 B2 | 9/2006 | Jia et al. | |
| 7,124,894 B1 | 10/2006 | Dobos | |
| 7,143,462 B2 | 12/2006 | Hohlbein | |
| 7,192,611 B2 | 3/2007 | Jia et al. | |
| 7,201,527 B2 | 4/2007 | Thorpe et al. | |
| 7,281,670 B2 | 10/2007 | Lakatos et al. | |
| 7,282,181 B2 | 10/2007 | Hudak et al. | |
| 7,303,143 B2 | 12/2007 | Davis et al. | |
| 7,311,456 B1 | 12/2007 | Neal | |
| 7,322,067 B2 | 1/2008 | Hohlbein | |
| 7,449,001 B2 | 11/2008 | Stoltz | |
| 7,478,960 B2 | 1/2009 | Glover | |
| 7,514,469 B2 | 4/2009 | Jia | |
| 7,596,974 B2 | 10/2009 | Smith et al. | |
| 7,699,608 B2 | 4/2010 | Han et al. | |
| 7,794,656 B2 | 9/2010 | Liang et al. | |
| 7,806,125 B2 | 10/2010 | Coopersmith | |
| 7,845,042 B2 | 12/2010 | Moskovich et al. | |
| 7,845,944 B2 | 12/2010 | DiGasbarro | |
| 2001/0002228 A1 | 5/2001 | Owens | |
| 2002/0088473 A1 | 7/2002 | Fonseca et al. | |
| 2003/0045814 A1 | 3/2003 | Sangha | |
| 2003/0049327 A1 | 3/2003 | Zanone et al. | |
| 2003/0053938 A1 | 3/2003 | Szeles | |
| 2003/0086743 A1 | 5/2003 | Gruenbacher et al. | |
| 2003/0120180 A1 | 6/2003 | Kaylor et al. | |
| 2003/0157206 A1 | 8/2003 | Paek | |
| 2003/0194678 A1 | 10/2003 | Viltro et al. | |
| 2003/0224320 A1 | 12/2003 | Kandelman et al. | |
| 2004/0020508 A1 | 2/2004 | Earl | |
| 2004/0082878 A1 | 4/2004 | Baldwin et al. | |
| 2004/0097834 A1 | 5/2004 | Stoltz | |
| 2004/0182414 A1 | 9/2004 | Puskas | |
| 2004/0220498 A1 | 11/2004 | Li et al. | |
| 2004/0226575 A1 | 11/2004 | Hampton | |
| 2004/0237226 A1 * | 12/2004 | Hohlbein et al. | 15/22.1 |
| 2004/0255416 A1 * | 12/2004 | Hohlbein | 15/106 |
| 2005/0019087 A1 | 1/2005 | Tsaur | |
| 2005/0026103 A1 | 2/2005 | Wasylucha | |
| 2005/0091769 A1 | 5/2005 | Jimenez et al. | |
| 2005/0115011 A1 | 6/2005 | Petit | |
| 2005/0147461 A1 | 7/2005 | Glover | |
| 2005/0201812 A1 | 9/2005 | Wong et al. | |
| 2005/0217688 A1 | 10/2005 | Liu et al. | |
| 2005/0218033 A1 | 10/2005 | Curtis | |
| 2005/0220530 A1 | 10/2005 | Carmona | |
| 2005/0221401 A1 | 10/2005 | Nomura et al. | |
| 2005/0233279 A1 | 10/2005 | Zeh et al. | |
| 2005/0244794 A1 | 11/2005 | Kemp et al. | |
| 2006/0026784 A1 | 2/2006 | Moskovich et al. | |
| 2006/0141421 A1 | 6/2006 | Braunecker et al. | |
| 2006/0225744 A1 | 10/2006 | Braunecker et al. | |
| 2006/0228163 A1 | 10/2006 | McSweeny | |
| 2006/0280548 A1 | 12/2006 | Sharpe | |
| 2007/0020032 A1 | 1/2007 | Abbas | |
| 2007/0086831 A1 | 4/2007 | Wold | |
| 2007/0101525 A1 | 5/2007 | Hohlbein | |
| 2007/0151575 A1 | 7/2007 | DeMasi | |
| 2007/0154863 A1 | 7/2007 | Cai et al. | |
| 2007/0173738 A1 | 7/2007 | Stoltz | |
| 2007/0183838 A1 | 8/2007 | Umar | |
| 2007/0223988 A1 | 9/2007 | Gruenbacher et al. | |
| 2007/0255177 A1 | 11/2007 | Pronovost | |
| 2008/0014010 A1 * | 1/2008 | Bartschi et al. | 401/146 |
| 2008/0034524 A1 | 2/2008 | Takahashi | |
| 2008/0044791 A1 | 2/2008 | Tsurukawa et al. | |
| 2008/0176183 A1 | 7/2008 | Gatzemeyer et al. | |
| 2008/0201884 A1 | 8/2008 | Vazquez et al. | |
| 2009/0012425 A1 | 1/2009 | Dodge et al. | |

| | | | |
|---|---|---|---|
| 2009/0052972 A1 | 2/2009 | DellaCorte | |
| 2009/0060622 A1 | 3/2009 | Lian et al. | |
| 2009/0180826 A1 | 7/2009 | Guay | |
| 2009/0205674 A1 | 8/2009 | Saloff et al. | |
| 2009/0258326 A1 | 10/2009 | Al-Sulaiman et al. | |
| 2009/0261179 A1 | 10/2009 | Hall | |
| 2009/0317340 A1 | 12/2009 | Pak | |
| 2009/0320226 A1 | 12/2009 | Robinson et al. | |
| 2010/0331725 A1 | 12/2010 | Libby et al. | |

FOREIGN PATENT DOCUMENTS

| | | |
|---|---|---|
| DE | 3832520 | 4/1990 |
| DE | 4139141 | 6/1993 |
| DE | 10035214 A1 | 2/2002 |
| DE | 202004008909 | 9/2004 |
| EP | 0092359 | 10/1983 |
| EP | 0097904 | 1/1984 |
| EP | 0244363 | 11/1987 |
| EP | 0373758 | 6/1990 |
| EP | 0631771 | 1/1995 |
| EP | 1053744 | 11/2000 |
| EP | 1095660 | 5/2001 |
| EP | 1270580 | 1/2003 |
| EP | 1639913 | 3/2006 |
| EP | 1639913 A1 | 3/2006 |
| EP | 2174649 | 4/2010 |
| FR | 2452277 | 10/1980 |
| FR | 2777459 | 10/1999 |
| GB | 842965 | 8/1960 |
| GB | 2205280 | 12/1988 |
| GB | 2394653 | 5/2004 |
| GB | 2394653 A | 5/2004 |
| GB | 2430146 | 3/2007 |
| JP | 1-097406 | 4/1989 |
| JP | 2-43099 | 2/1990 |
| JP | 2-152405 | 6/1990 |
| JP | 2-297498 | 12/1990 |
| JP | 9-215524 | 8/1997 |
| JP | 2003-019023 | 1/2003 |
| JP | 2003-250631 | 9/2003 |
| JP | 2004-108858 | 4/2004 |
| JP | 2005-257604 | 9/2005 |
| KR | 20-0183429 | 5/2000 |
| NL | 9400631 | 12/1995 |
| RU | 2105519 | 2/1998 |
| RU | 2239342 | 11/2004 |
| TW | 200605814 | 2/2006 |
| WO | WO 92/10146 | 6/1992 |
| WO | WO 95/17159 | 6/1995 |
| WO | WO 99/05987 | 2/1999 |
| WO | WO 01/62082 | 8/2001 |
| WO | WO 03/00506 | 1/2003 |
| WO | WO 2004/084752 | 10/2004 |
| WO | WO 2005/009352 | 2/2005 |
| WO | WO 2006/019289 | 2/2006 |
| WO | WO 2006/032367 | 3/2006 |
| WO | WO 2007/011552 | 1/2007 |
| WO | WO 2007/073917 | 7/2007 |
| WO | WO 2008/091935 | 7/2008 |
| WO | WO 2011/106017 | 9/2011 |

OTHER PUBLICATIONS

Office Action from the Taiwan Intellectual Property Office, dated Apr. 7, 2011, for corresponding Taiwan Patent Application No. 97102421.

International Search Report and Written Opinion of corresponding International Application No. PCT/US2010/025605 dated Nov. 19, 2010.

International Search Report and Written Opinion of International Application No. PCT/US2008/051778 dated Dec. 12, 2008.

International Search Rpeort and Written Opinion of International Application No. PCT/US2011/027042 mailed Nov. 28, 2011.

Written Opinion in International Application No. PCT/US11/027042, mailed Jul. 10, 2012.

Written Opinion for PCT/US2010/025605 mailed on Mar. 1, 2012.

Anonymous, 2008, "Salviathymol N".

Anonymous, 2012, "Betaisodona-Mund-Antiseptikum".

Ciobanu et al., "Antimicrobial Mouthwash Concentrate—Inhibiting Cariogenic Buccal Flora Comprises Alcoholic Extract of Plants, Volatile Oils and Propolis Tincture," WPI Thomson AN 1993-203503.

Hyssopbrush, 2013, product description on CDM Supply website, http://cdmsupply.com/product_info.php?cPath=44&products_id=130.

International Search Report and Written Opinion in International Application No. PCT/US10/043825, mailed Apr. 28, 2011.

International Search Report and Written Opinion in International Application No. PCT/US11/027740, mailed Jan. 17, 2012.

International Search Report and Written opinion in International Application No. PCT/US2009/054582, mailed Aug. 3, 2010.

Squirtbrush, 2013, product description on CDM Supply website, http://cdmsupply.com/product_info.php?cPath=42 &products_id=109.

* cited by examiner

US 8,517,728 B2

ORAL CARE IMPLEMENT HAVING FLUID DELIVERY SYSTEM

FIELD OF INVENTION

The present invention is directed to an oral care implement including a capillary delivery system for a fluid.

BACKGROUND OF THE INVENTION

Oral care implements, particularly toothbrushes, are typically used by applying toothpaste to a bristle section followed by brushing regions of the oral cavity, e.g., the teeth, tongue, and/or gums. Some toothbrushes have been equipped with fluid reservoirs and systems for delivering auxiliary active agents, such as whitening agents, breath freshening agents, and the like. There is a continuing need for alternative oral care implements for delivering auxiliary active agents.

BRIEF SUMMARY OF THE INVENTION

The present invention pertains to an oral care implement having a capillary delivery system. Optionally, the oral care implement has a head containing tooth cleaning elements on a first surface thereof.

In one embodiment, an oral care implement includes a reservoir containing at least one active agent. A variety of active agents can be administered for therapeutic, hygienic, and/or other benefits, such as fresh breath, tooth whitening, or producing sensations of heat, cool, or tingling.

In another embodiment, an oral care implement includes a capillary channel extending through at least a portion of the implement to deliver the active agent to one or more outlets. In one embodiment, an outlet is located on a second surface of the head generally opposite the first surface that contains the tooth cleaning elements.

In yet another embodiment, an oral care implement has a head containing tooth cleaning elements, a reservoir for storing a fluid containing at least one active agent, and an overflow chamber. The reservoir and overflow chamber may be separated by a partition. A capillary channel constructed from a fibrous material, ceramic, porous plastic, or combination thereof extends through at least a portion of the implement to deliver the active agent to one or more outlets.

In another embodiment, an oral care implement has a head containing tooth cleaning elements, a reservoir containing at least one active agent, a capillary channel extending through at least a portion of the implement to deliver the active agent to one or more outlets, and a motion-producing device. When activated, the motion-producing device vibrates the implement or a portion thereof, such as the head portion. The vibration enhances the function of the tooth cleaning elements and also promotes delivery of the active agent through the capillary channel, which together provides an enhanced cleaning action.

BRIEF DESCRIPTION OF THE DRAWINGS

The features, and advantages of the invention will be apparent from the following more detailed description of certain embodiments of the invention and as illustrated in the accompanying drawings in which.

DETAILED DESCRIPTION OF THE INVENTION

Figure 1:
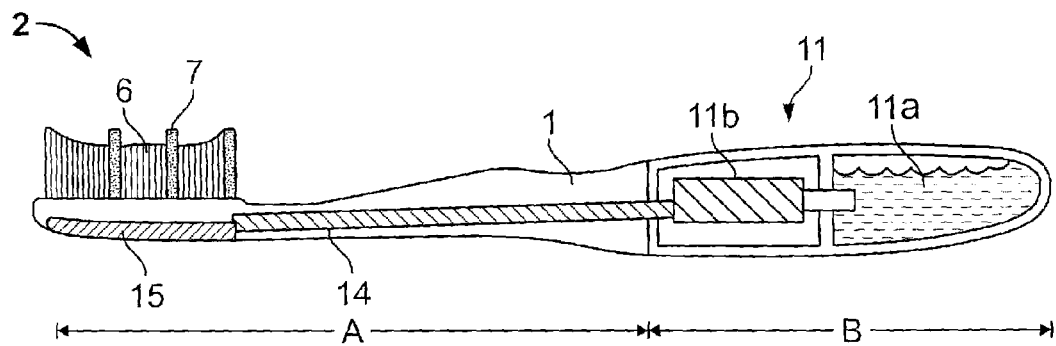
FIG. 1 is a schematic illustration of a toothbrush according to one embodiment of the invention.
Figure 2:
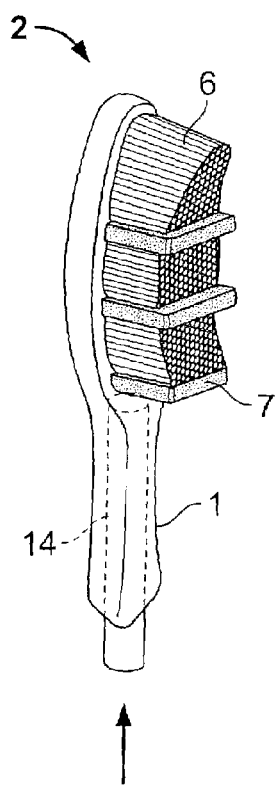
FIG. 2 is a front perspective view of the head of the toothbrush shown in FIG. 1.
Figure 3:
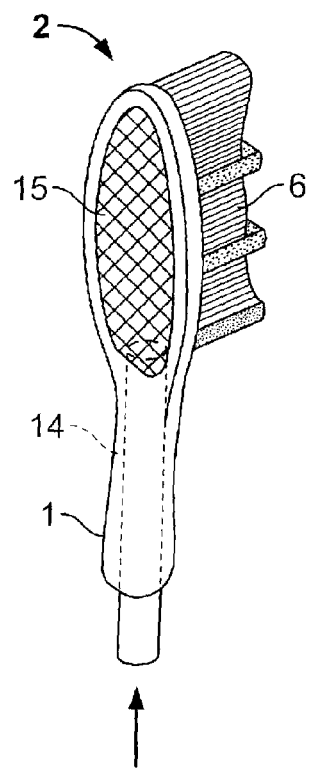
FIG. 3 is a rear perspective view of the head of the toothbrush shown in FIG. 1.

FIG. 1 schematically illustrates a toothbrush having a handle 1 and a head 2 containing one or more tooth cleaning elements, such as bristles 6 and/or elastomeric cleaning elements 7. A reservoir 11 is provided for storing a medium containing an active agent. The medium is most often in the form of a liquid, but can be in other forms, e.g., semi-solid, paste, or gel. The reservoir 11 can include a liquid storage tank 11a in fluid communication with a delivery section 11b. A capillary channel 14 generally extends in the longitudinal direction of the toothbrush for delivering the active agent from the reservoir 11 to at least one outlet 15.

In one aspect, the outlet 15 can be located on a surface of the head 2 generally opposite the surface that contains the tooth cleaning elements 6 and 7. In another aspect, the outlet 15 can be located within the bristles 6 and/or elastomeric cleaning elements 7. Optionally, a plurality of outlets may be provided on both the surface of the head that contains the tooth cleaning elements as well as the opposite the surface of the head, e.g., for delivering the same active agent from a common supply or different active agents from separate supplies.

The channel 14 uses capillary action to draw liquid from the reservoir 11 to the outlet 15. The outlet 15 can be configured as a non-woven pad, membrane or other structure that allows passage of the medium containing the active agent. Examples of materials that can be used for the outlet include porous plastics and other porous materials, such as those described below with reference to the capillary channel 14.

The capillary channel 14 generally has a capillary structure and usually is a porous material. Examples of suitable materials include fibrous materials, ceramics, and porous plastics such as those available from Porex Technologies, Atlanta, Ga. One example of a fibrous material is an acrylic material identified as type number C10010, available from Teibow Hanbai Co., Ltd., Tokyo, Japan. A mixture of porous and/or fibrous materials may be provided which have a distribution of larger and smaller capillaries. The channel can be formed from a number of small capillaries that are connected to one another, or as a larger single capillary tube.

The reservoir 11 may be formed from any suitable material and may include reticulated foam, which may range from hydrophilic to hydrophobic. Hydrophobic foams may be used with non-water based liquids. An example of a reticulated foam is Bulpren S90, manufactured by Recticel (Wetteren, Belgium). Bulpren S90 is an open cell polyurethane foam based on polyester which averages 90 pores per inch. Other examples of materials that can be used for the reservoir 11 include ceramics and porous plastics.

Non-limiting examples of capillary configurations that can be used are shown in FIGS. 4-7. The capillary devices 10 generally have a housing 20 that includes a reservoir 11 for storing fluid 13 and an overflow chamber 25. The reservoir 11 and overflow chamber 25 may be separated by a partition 21, for example, or otherwise separated such as described below with reference to FIG. 7. The reservoir 11 may be an integral part of housing 20 or a separate element connected to the housing. An inlet 22 allows air to flow freely into and out of overflow chamber 25.

Partition 21 may include an opening 12 which is closed by the capillary channel 14. The channel 14 generally extends from the opening 12 to the outlet 15 and is in direct contact with a capillary storage 16. The average capillarity of the capillary storage 16 is generally smaller than the average capillarity of channel 14. Although the capillary storage is arranged about the periphery of capillary channel 14, it does not necessarily extend all the way around the channel. Strict separation of capillary storage 16 and channel 14 is not necessary.

The capillary channel 14 can be press-fit into an opening in the handle 1 or, alternatively, the handle 1 can be overmolded around the capillary channel 14. The capillary channel 14 generally provides the only path by which air can enter the otherwise closed reservoir 11. The finer capillaries of channel 14 transfer fluid to the outlet 15. The larger capillaries allow air to enter the reservoir 11. In general, air can enter through at least the largest capillary in the channel.

Figure 5:
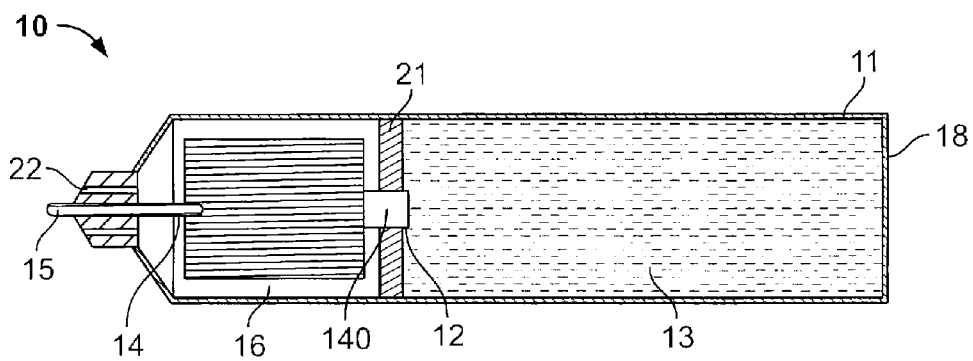

With reference to FIG. 5, by way of example, when air expansion takes place within the reservoir 11, a portion of the fluid 13 in the reservoir 11 will be transferred through an opening 12 and channel 14 into the normally fluid-free portions of capillary storage 16. In other words, capillary storage 16 receives excess fluid and prevents uncontrolled leakage of the fluid from the outlet 15, or other portions of the implement. The excess fluid in capillary storage 16 will return to the reservoir 11 through channel 14 when the pressure in the reservoir 11 subsides. This process is repeated whenever temperature fluctuations, for example, cause air volume fluctuations within the reservoir 11. As the fluid stored in capillary storage 16 is always returned to reservoir 11, the capillary storage will not already be filled to capacity when there is an air expansion. Also, even though channel 14 is continuously wetted with fluid, at least in the area of opening 12, air cannot interrupt the return of the fluid 13 to the reservoir 11 as long as there is fluid in the capillaries of the storage 16 which are larger than the largest pore in the channel 14.

Figure 4:
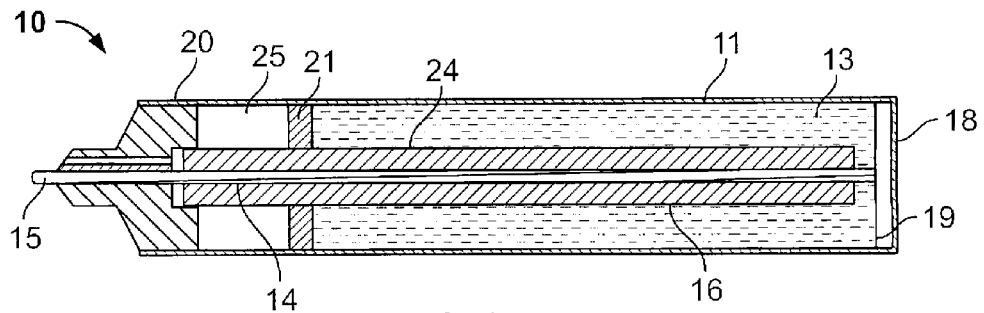
FIGS. 4-7 show examples of capillary configurations that can be used with the oral care implement.
Figure 6:
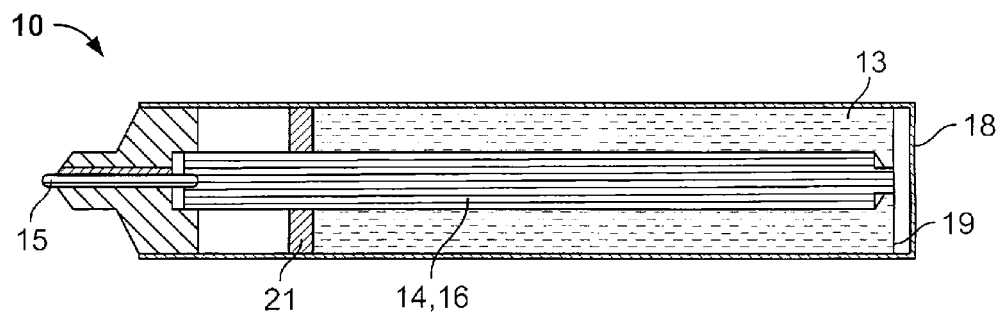
Figure 7:
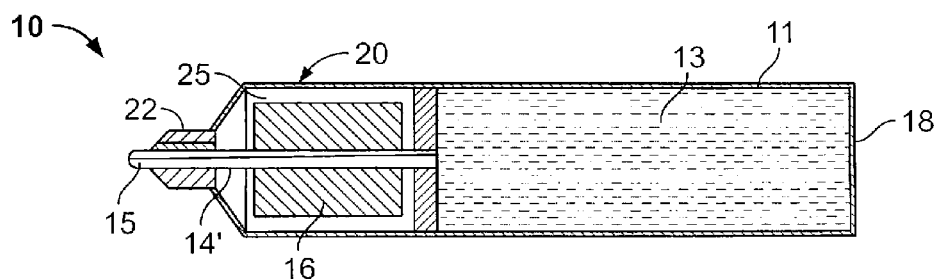

Although the outlet 15 is illustrated in FIGS. 1, 3, 5, and 6 as a separate element from the channel 14, it should be recognized that the outlet 15 may alternatively be integral with the channel 14, as schematically shown in FIGS. 4 and 7. When the outlet 15 is formed from a porous material, its pores generally should be smaller than those of the channel 14 to ensure that the fluid in the channel 14 will flow toward the outlet 15 during dispensing. With reference to FIGS. 4 and 6, channel 14 may be configured so that it extends into area 19 near the reservoir base 18. In this type of configuration, the capillary storage and the capillary channel 14 usually are enclosed by a tube 24. The tube 24 provides additional protection against unwanted leakage.

In the configuration shown in FIG. 4, capillary storage 16 and capillary channel 14 are separate structural elements and the channel 14 extends into base area 19. In the configuration shown in FIG. 6, a mixture of porous materials having the requisite combination of capillary sizes form a unitary capillary storage 16 and channel 14.

In the configuration shown in FIG. 5, channel 14 and capillary storage 16 define a unitary structural element similar to that shown in FIG. 6. The rear portion 140 of the integral channel and capillary storage is tapered so that it may be received in opening 12. To ensure that there is a sufficient amount of fine, fluid transferring capillaries in the opening 12, this portion of the combined channel/storage may be pinched together at the opening in a defined manner. The rear portion 140 may also be provided as a separate element that is connected to the capillary storage.

As shown, for example, in FIG. 7, capillary channel 14' may be configured so that it includes a radially extending portion that separates the reservoir 11 from the overflow chamber 25. The channel 14' and radially extending portion fill the opening between the reservoir 11 and the overflow chamber 25. The pores in the radially extending portion may be substantially similar to those in the channel 14' and allow air to pass, but block the flow of fluid. As a result, the radially extending portion may be used to regulate the flow of air into the channel 14'.

Examples of capillary fluid systems of this general type are shown, for example, in U.S. Pat. Nos. 5,102,251; 5,352,052; 6,089,776; 6,095,707; 6,164,858; 6,183,155; 6,322,268; and 6,497,527, the disclosures of which are hereby incorporated by reference.

In another aspect, a vibratory device can be provided to vibrate the toothbrush or a portion thereof, such as the head 2 or a portion thereof. The vibration-producing device can be used to vibrate tooth cleaning elements 6 and 7 and/or soft tissue cleaning elements while, at the same time, promote delivery of the active agent(s) through the capillary channel 14 to provide an enhanced cleaning action.

A wide variety of vibratory devices can be used to produce vibrations over a wide range of frequencies to meet the needs of a particular application. Various types of vibratory devices are commercially available, such as transducers. One example of a vibratory device provides frequencies in the range of about 100 to 350 kHz. The vibration frequencies may be of different waveforms, including sinusoid, square, sawtooth and the like. Nevertheless, other values and waveforms are possible. A vibratory device may be located in head of the toothbrush or neck thereof. When activated, vibratory device is powered by battery (and controlled by electronics on circuit board or switching system) so as to induce vibrations in head of the toothbrush and thereby enhances teeth-cleaning action imparted by the tooth cleaning elements. In alternate embodiments, a vibratory device may include a micro motor attached to a shaft, with the shaft coupled to an eccentric rotating about an axis parallel to the longitudinal axis of the toothbrush. In still other embodiments, a vibratory-producing device includes an eccentric that is driven by a micro motor in a translatory manner.

A switch, such as a button, toggle switch, rotating dial, or the like, can be provided for activating the vibratory device. A vibratory device often has a power source, such as a battery. Activating the switch can cause the vibration-producing device to operate for a user-defined interval (e.g., during the time that a button is depressed or a switch is in an engaged position), or alternatively can activate a timing circuit that causes the vibratory device to operate for a predetermined interval. If a timing circuit is used, the associated interval either may be preset or may be adjustable, e.g., by a user-activated rotating dial.

Additional embodiments of the invention include configurations of vibratory device(s), bristles (or other tooth cleaning elements) and other components as described in U.S. patent application Ser. No. 10/768,363 (filed Jan. 30, 2004 and titled "Toothbrush with Enhanced Cleaning Effects"), published as U.S. Pat. Pub. No. 20050091769A1, incorporated by reference herein. For example, the neck portion of the toothbrush can be provided with neck-part zones made of an elastically relatively compliant material so as to increase the elasticity of the neck part. This would permit the head, during use of the toothbrush, to be forced back resiliently in the case of forces acting in the direction of the brushing surface. Optionally, the neck-part zones could be designed as notches which extend over part of the neck circumference and are filled with elastically compliant material (e.g. with thermoplastic elastomer).

The outlet 15 can be incorporated into an elastomeric material to provide a tissue cleanser, which can be used, for example, for cleaning the tongue, cheeks, lips, and/or gums. A tissue cleaner may employ a variety of suitable biocompatible resilient materials, such as elastomeric materials. To provide optimum comfort as well as cleaning benefits, an elastomeric material usually has a hardness property in the range of A8 to A25 Shore hardness, such as styrene-ethylene/butylene-styrene block copolymer (SEBS), available from GLS Corporation.

A tissue cleanser can be configured with a multiplicity of tissue engaging elements, which can be formed as nubs. As used herein, a "nub" is generally meant to include a column-like protrusion (without limitation to the cross-sectional shape of the protrusion) which is upstanding from a base surface. In general, the nub can have a height that is greater than the width at the base of the nub as measured in the longest direction. Nubs also can include projections wherein the widths and heights are roughly the same or wherein the heights are somewhat smaller than the base widths.

Such tissue engaging elements can help reduce a major source of bad breath and improve hygiene. Nubs enable removal of microflora and other debris from the tongue and other soft tissue surfaces within the mouth. The tongue, in particular, is prone to develop bacterial coatings that are known to harbor organisms and debris that can contribute to bad breath. This microflora can be found in the recesses between the papillae on most of the tongue's upper surface as well as along other soft tissue surfaces in the mouth. When engaged or otherwise pulled against a tongue surface, for example, the nubs of elastomeric tissue cleanser can provide for gentle engagement with the soft tissue while reaching downward into the recesses of adjacent papillae of the tongue. The elastomeric construction of a tissue cleanser also enables the base surface to follow the natural contours of the oral tissue surfaces, such as the tongue, cheeks, lips, and gums of a user. In addition, the soft nubs are able to flex as needed to traverse and clean the soft tissue surfaces in the mouth along which it is moved.

The nubs often are conically shaped, such as in the shape of a true cone, frusto-conically shaped elements, and other shapes that taper to a narrow end and thereby resemble a cone irrespective of whether they are uniform, continuous in their taper, or have rounded cross-sections. The smaller width or diameter of the tip portion in conjunction with the length of the conically shaped nub enable the nubs to sweep into the recesses of the tongue and other surfaces to clean the microbial deposits and other debris from the soft tissue surfaces. The nubs also are able to flex and bend from their respective vertical axes as lateral pressure is applied during use. This flexing enhances the comfort and cleaning of the soft tissue surfaces. Alternatively, tissue cleaning elements may have other shapes. As one example, the tissue cleanser may have different forms, including grated forms, such as described in co-pending U.S. patent application Ser. No. 11/566,479, filed Dec. 4, 2006, which is incorporated herein by reference.

The medium containing the active agent can be incorporated into a sealed reservoir 11 during manufacture of the toothbrush, in which case the toothbrush can be disposed of after the supply of the active agent is exhausted. Alternatively, the reservoir 11 can be refillable through an inlet (not shown), and/or can be replaceable, e.g., by inserting a replaceable cartridge into a recess in the toothbrush. The cartridge can be spring-loaded to stay in place after insertion, and can have a seal to prevent unwanted leakage of the active agent.

As illustrated in FIG. 1, the toothbrush can comprise a brush section A and a reservoir section B that are joined to each other, e.g., by threaded engagement, snap-fitting, or the like. The reservoir section B can be disposable, refillable, and/or interchangeable with other reservoir sections B containing different active agents, for example.

Optionally, a user-activated switch, such as a dial (not shown), can have multiple settings for selecting one or more of several active agents. For example, the dial can have a first setting for oxidizer/whitener treatment, a second setting for breath freshener treatment, and a third setting for antimicrobial treatment. The toothbrush can be supplied in the form of a kit including a toothbrush or a brush section A thereof, and one or more cartridges or reservoir sections B containing active agent(s). Multiple cartridges can be provided, for example, for supplying different active agents or a replacement supply of the same active agent.

In FIG. 1, a toothbrush is shown schematically having a head 2, bristles 6, and a handle 1. It should be understood that any bristle configuration and any handle configuration can be used, and the present invention should not be regarded as being limited to any particular configuration.

The toothbrush can be used by brushing the teeth or gums using bristles 6 and/or other tooth cleaning elements and/or by massaging the tongue, gums, or other regions of the oral cavity with a tissue cleanser. The active agent can be administered through one or more outlets present in or near the tooth cleaning elements and/or within the tissue cleanser and/or on other locations on the toothbrush. Depending on the type of active agent used and the location of the outlet(s), the active agent can be administered before, during, or after brushing.

Non-limiting examples of active agents which can be used include antibacterial agents, whitening agents, anti-sensitivity agents, anti-inflammatory agents, anti-attachment agents, plaque indicator agents, flavorants, sensates, and colorants. Examples of these agents include metal ion agents (e.g., stannous ion agents, copper ion agents, zinc ion agents, silver ion agents) triclosan; triclosan monophosphate, chlorhexidine, alexidine, hexetidine, sanguinarine, benzalkonium chloride, salicylanilide, domiphen bromide, cetylpyridinium chloride, tetradecylpyridinium chloride, N-tetradecyl-4-ethylpyridinium chloride (TDEPC), octenidine, delmopinol, octapinol, nisin, essential oils, furanones, bacteriocins, flavans, flavinoids, folic acids, vitamins, hydrogen peroxide, urea peroxide, sodium percarbonate, PVP—$H_2O_2$, polymer-bound perxoxides, potassium nitrates, occluding agents, bioactive glass, arginine salts, arginine bicarbonate, bacalin, polyphenols, ethyl pyruvate, guanidinoethyl disulfide, tartar control agents, anti-stain ingredients, phosphate salts, polyvinylphosphonic acid, PVM/MA copolymers; enzymes, glucose oxidase, papain, ficin, ethyl lauroyl arginate, menthol, carvone, and anethole, various flavoring aldehydes, esters, and alcohols, spearmint oils, peppermint oil, wintergreen oil, sassafras oil, clove oil, sage oil, eucalyptus oil, marjoram oil, cinnamon oil, lemon oil, lime oil, grapefruit oil, and/or orange oil.

The active agent and/or its medium can be selected to complement a toothpaste formula, such as by coordinating flavors, colors, aesthetics, or active ingredients. A flavor can be administered to create a gradual flavor change during brushing, which presently is not possible using toothpaste alone.

The active agent may be compatible with toothpaste, or may be unstable and/or reactive with typical toothpaste ingredients. The active agent also may be a tooth cleaning agent to boost the overall efficacy of brushing.

The active agent can be provided in any suitable vehicle, such as in aqueous solution or in the form of gel or paste. Non-limiting examples of vehicles include water, monohydric alcohols such as ethanol, poly(ethylene oxides) such as polyethylene glycols such as PEG 2M, 5M, 7M, 14M, 23M, 45M, and 90M available from Union Carbide, carboxymethylene polymers such as Carbopol® 934 and 974 available from B.F. Goodrich, and combinations thereof. The selection of a suitable vehicle will be apparent to persons skilled in the art depending on such factors as the properties of the active agent and the desired properties of the medium, such as viscosity. Examples of tooth whitening compositions are described in U.S. Pat. Nos. 6,770,266 and 6,669,930, the disclosures of which are hereby incorporated by reference.

The reservoir 11 can contain a quantity of the active agent medium intended for a single use or a small number of uses, or may facilitate repeated use over an extended period of time, e.g., up to several months or several years. The size of the reservoir 11 can be selected to be compatible with the desired overall dimensions of the toothbrush as well as such factors as the stability of the active agent and the quantity of medium administered during each application.

The supply of active agent in the reservoir 11 generally is free or substantially free of components which are incompatible with the active agent and/or the medium containing the active agent, such as incompatible toothpaste components as previously identified.

The toothbrush optionally can be provided with compartments and/or access panels for access to the various components, such as the power source and reservoir. The power source can be, for example, a replaceable or rechargeable battery as well known.

FIGS. 8-13 illustrate an oral care implement, such as a toothbrush 100, having a handle 103 and a head 105 which may be used for cleaning the teeth and soft tissue in the mouth, such as the tongue, interior surfaces of the cheeks, lips or the gums. Handle 103 is provided for the user to readily grip and manipulate the toothbrush, and may be formed of many different shapes and constructions. While the head is normally widened relative to the neck of the handle, it could in some constructions simply be a continuous extension or narrowing of the handle. The head 105 can have a first face 106 that supports tooth cleaning elements 107 (FIGS. 12 and 13) and a second face 108 that supports a tissue cleanser 300 (FIGS. 9 and 10), which can have one or more outlets for dispensing active agent(s) as previously described. The first and second faces 106, 108 can be disposed on opposite sides of head 105. Nevertheless, tissue cleanser 300 may be mounted elsewhere, such as the proximal end 104 of handle 103. The tissue cleanser 300 or portions of it may also be located on the peripheral sidewall surface 101 of head 105 or extend farther towards the proximate end 104 of handle 103 than illustrated.

Tissue cleanser 300 can be configured with a multiplicity of tissue engaging elements 303 (FIGS. 8-12), which can be formed as nubs.

Figure 9:
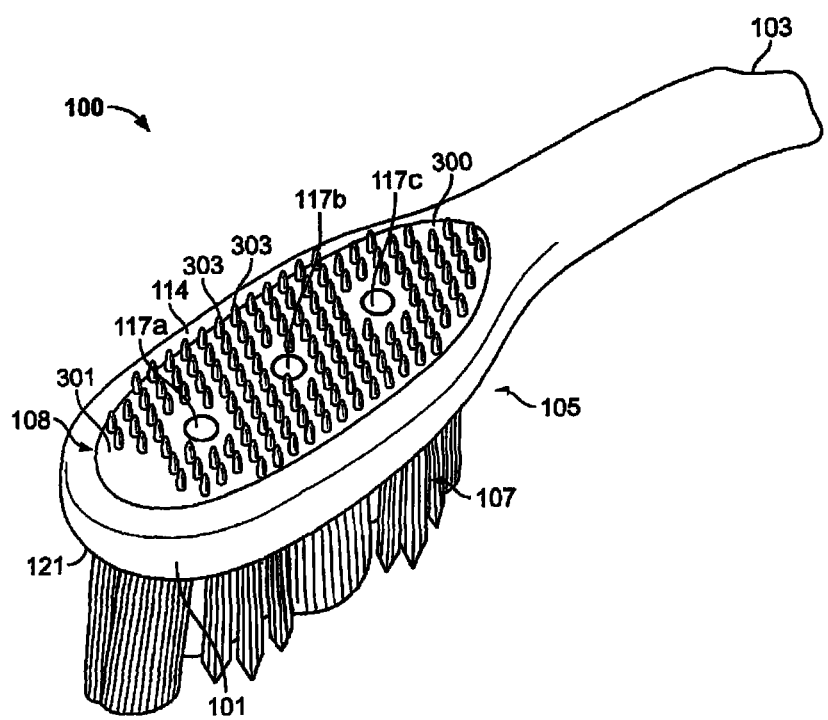
FIG. 9 is an enlarged perspective view of a head of an oral care implement of FIG. 8.
Figure 11:
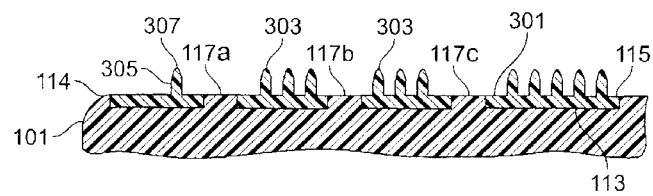
FIG. 11 is a partial section view of a head of the oral care implement of FIG. 8 taken along line 4-4 of FIG. 10.

As seen in FIGS. 9 and 11, the nubs 303 can be conically shaped. With reference to FIG. 11, the base portion 305 of each conically shaped tissue engaging element 303 can be larger than the corresponding tip portion 307. In this conically shaped configuration, the base portion 305 has a wider cross-sectional area to provide effective shear strength to withstand the lateral movement of the tissue cleanser 300 along the surface of the tongue or other soft tissue surface.

Figure 10:
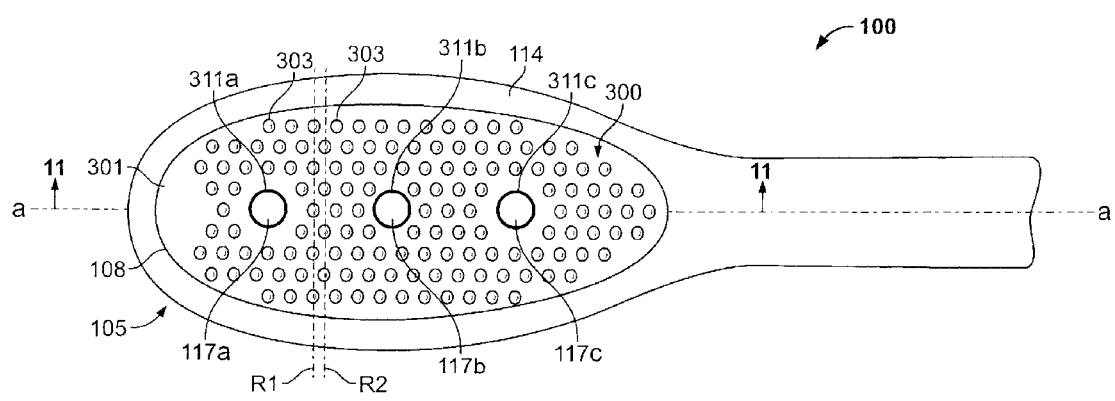
FIG. 10 is a plan view of the oral care implement of FIG. 8 illustrating a tongue cleaning feature.

As seen in FIG. 10, nubs 303 can be disposed in longitudinal rows in a direction generally parallel to the longitudinal axis a-a. Further, nubs 303 are disposed in transverse rows R1, R2 on an axis parallel to base surface 301 and generally perpendicular to the longitudinal axis a-a. Adjacent nubs 303 can be provided on the base surface 301 in a staggered arrangement. For example, adjacent transverse rows of nubs R1 and R2 can have nubs 303 that are not directly behind each other. A first nub is said herein to be "directly behind" second nub when it is located within the lateral bounds of the second nub extending in a longitudinal direction. This configuration enables improved cleaning of the soft tissue surfaces by facilitating the removal of microflora and other debris, and especially from the recesses of adjacent papillae of the tongue. Nonetheless, the nubs could be arranged randomly or in a myriad of different patterns.

Figure 8:
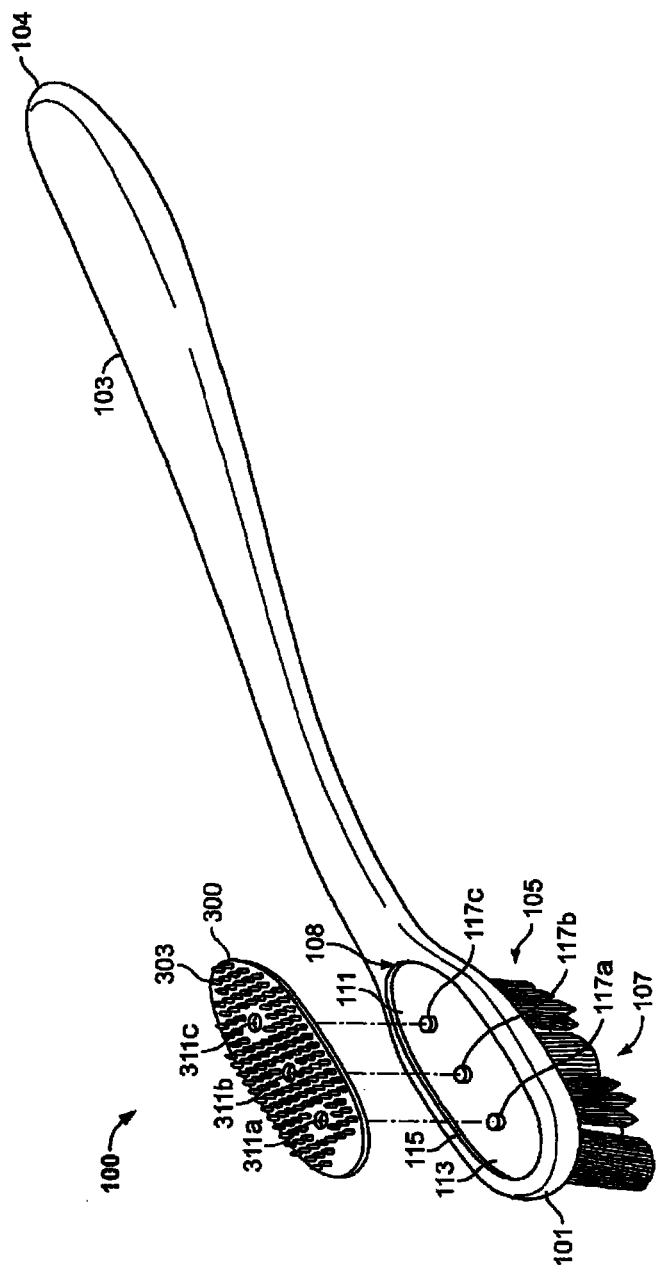
FIG. 8 is an exploded assembly perspective view of an oral care implement according to one or more aspects of an illustrative embodiment.

Tongue cleanser 300 can be formed by being molded to head 105, although other manufacturing processes could be used. With reference to FIGS. 8 and 11, tissue cleanser 300 can be molded within a basin or a receiving cavity 111 in face 108 of head 105. The receiving cavity 111 has a lower base surface 113 and a peripheral sidewall 115 extending away from the lower base surface 113. In one mounting arrangement, nubs 303 of the tissue cleanser 300 are exposed for use with the base surface of the tissue cleanser 300 being flush or recessed relative to the surface 114 of the head. Nevertheless, other orientations are possible. Also, base surface 301 of the tissue cleanser could be embedded in head 105 or covered by another layer with nubs 303 projecting through appropriate openings.

As can be seen in FIGS. 8 and 11, face 108 also can include one or more peg members 117a-c disposed within basin 111. Peg members 117 form anchor points against the opposing mold to prevent the head from moving under the pressure of the injection molding. As a result, tissue cleanser 300 can include one or more complementary apertures 311a-c which exposes the tops of peg members 117a-c. Although, the pegs are illustrated in alignment along the centerline of the head (e.g. longitudinal axis a-a), the pegs could have many different positions. Further, the pegs and basin can both be included with head 105, but either could be used without the other.

Alternatively, basin 111 and peg members 117a-c may be provided to position and hold a previously molded tissue cleanser, although these constructions are not necessary to use such a previously molded tissue cleanser.

Peg members 117a-c may take on a variety of shapes and lengths. With continued reference to the FIGS. 8 and 11, head 105 includes peg members 117a-c extending away from the lower base surface 113 of basin 111 to the height of the peripheral sidewall 115. The peg members 117a-c are shaped in the form of a cylinder, but other shapes and lengths of the peg members 117a-c are possible. While the molding process can be used to bond the tissue cleanser to the head, the tissue cleanser could be preformed and attached by adhesive or other known means.

As shown in FIGS. 8-11, tissue cleanser 300 can be formed as a pad composed of a soft and pliable elastomeric material for comfortable cleaning and effective removal of bacteria and debris disposed on the surface of the tongue, other soft tissue in the mouth and even along the lips, as well as for dispensing the active agent(s) as previously described. The tissue cleanser 300 also can provide effective massaging, stimulation and removal of bacteria, debris and epithelial cells from the surfaces of the tongue, cheeks, gums or lips.

Figure 12:
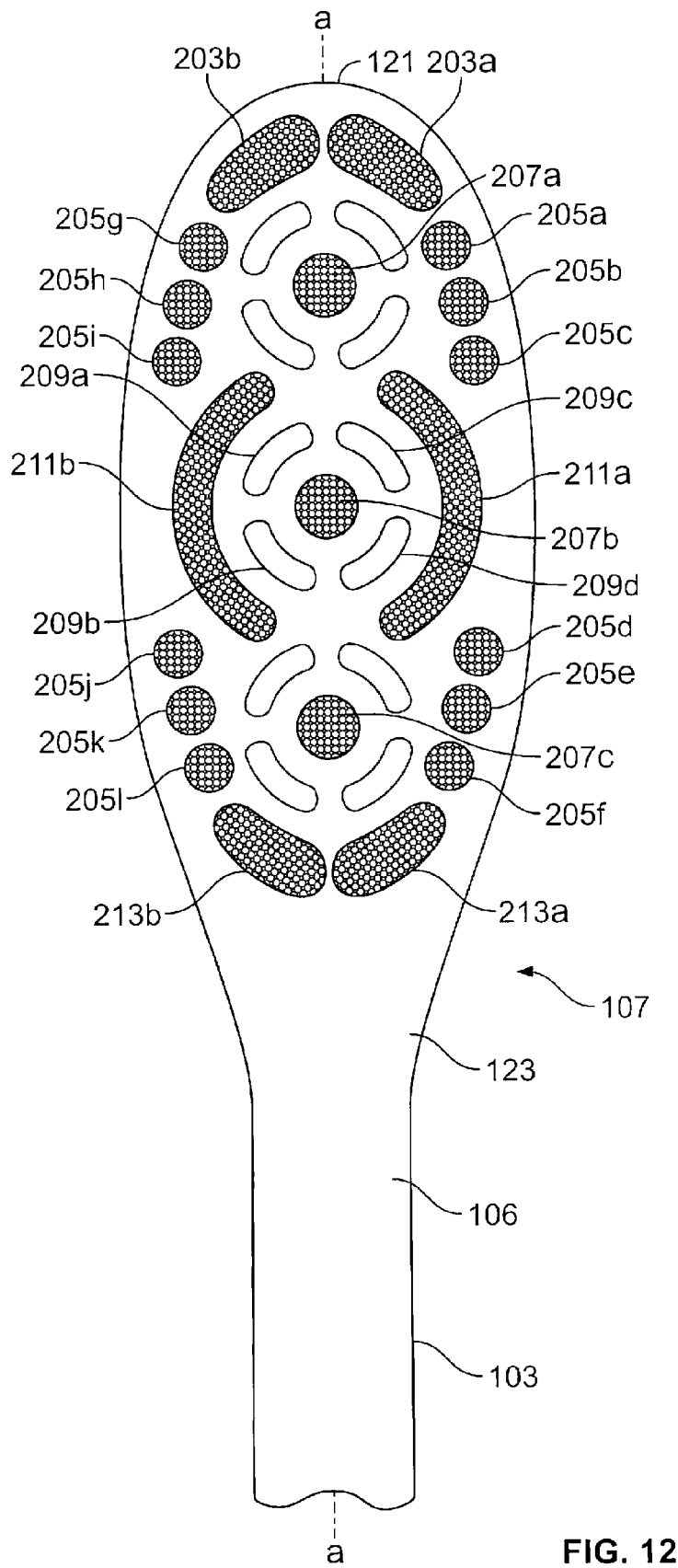
FIG. 12 is a plan view of the oral care implement of FIG. 8 illustrating at least one tooth cleaning configuration.
Figure 13:
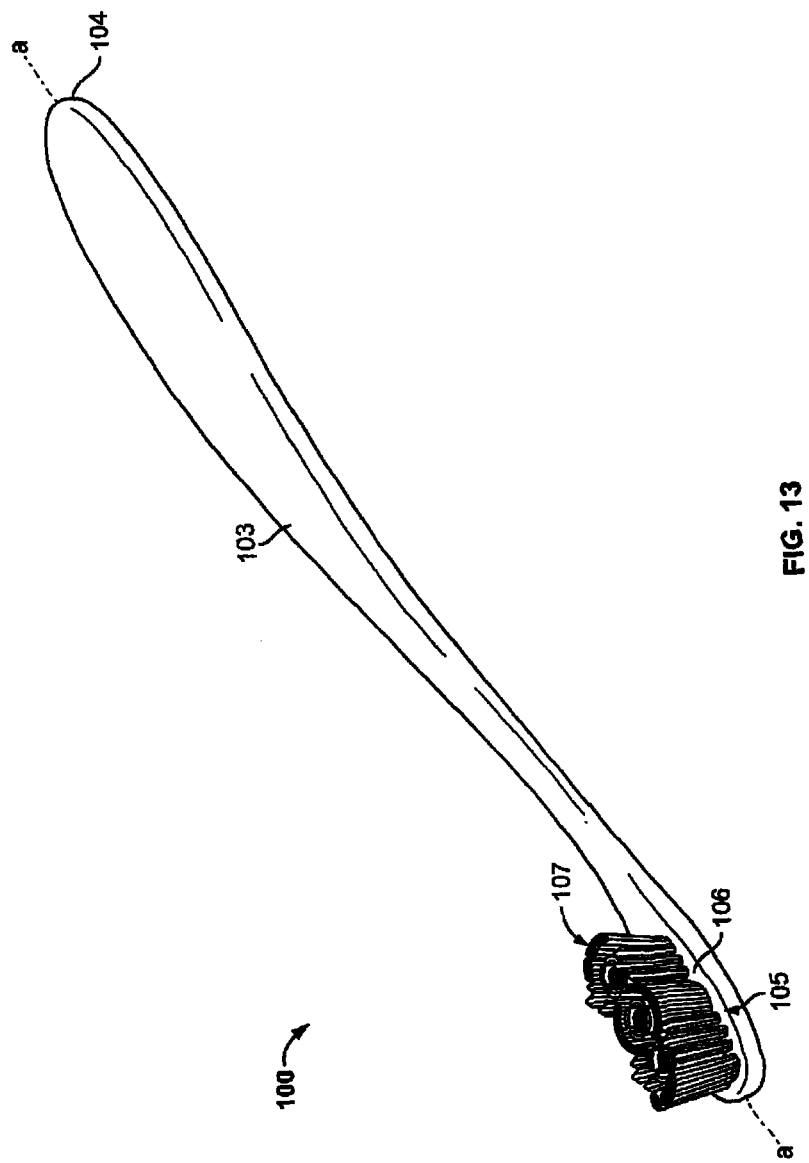
FIG. 13 is a perspective of the view of the oral care implement illustrating example tooth cleaning elements.

Referring to FIGS. 12 and 13, the tooth cleaning elements 107 of head 105 may include a variety of tooth cleaning elements which can be used for wiping, cleaning and massaging the user's teeth and gums. Any suitable form of tooth cleaning elements may be used. The term "tooth cleaning elements" is used in a generic sense which refers to filament bristles or elastomeric fingers or walls that have any desirable shape. In the illustrated example of FIG. 12, tooth cleaning elements 107 include distal tooth cleaning elements 203a-b disposed at a distal tip 121 of head 105, peripheral tooth cleaning elements 205a-l, longitudinal tooth cleaning elements 207a-c disposed along longitudinal axis a-a, arcuate tooth cleaning elements 209a-d and 211a-b, and proximal cleaning elements 213a,b. Tooth cleaning elements 205, 207, 211 and 213 can be provided as tufts of bristles whereas tooth cleaning elements 209 can be formed as elastomeric walls. Nevertheless, other forms and types of tooth cleaning elements may be used.

It will be understood that while the invention has been described in conjunction with specific embodiments thereof, the foregoing description and examples are intended to illustrate, but not limit the scope of the invention. Other aspects, advantages and modifications will be apparent to those skilled in the art to which the invention pertains, and these aspects and modifications are within the scope of the invention and described and claimed herein.

What is claimed is:

1. A toothbrush comprising:
   a handle,
   a head having a first surface containing at least one tooth cleaning element comprising bristles;
   a reservoir for storing an active agent;
   a porous outlet located on a second surface of the head opposite the first surface;
   a capillary channel that delivers the active agent from the reservoir to the porous outlet by capillary action, wherein the capillary channel is made of a porous material and is in continuous fluid communication with the porous outlet; and
   a soft tissue cleanser constructed of an elastomeric material positioned on the second surface of the head, the porous outlet incorporated into the soft tissue cleanser.

2. The toothbrush of claim 1, wherein the porous outlet comprises a non-woven pad or membrane through which the active agent can flow, and wherein the non-woven pad or membrane is constructed of a porous material having pores that are smaller than pores of the porous material of the capillary channel.

3. The toothbrush of claim 1, further comprising an active agent in the reservoir wherein the active agent is selected, from the group consisting of antibacterial agents; oxidative or whitening agents; supercharged fluoride delivery ingredients; tooth sensitivity ingredients; gum health actives; nutritional ingredients; tartar control or anti-stain ingredients; enzymes; sensate ingredients; flavors or flavor ingredients; anti-cavity or enamel repair agents; breath freshening ingredients; oral malodor reducing agents; anti-attachment agents; diagnostic solutions; occluding agents; and combinations thereof.

4. The toothbrush of claim 3, wherein the active agent is selected from the group consisting of (i) an antibacterial agent selected from the group consisting of chlorhexidine, cetyl pyridininum chloride, triclosan, and zinc salts; (ii) an oxidizing or whitening agent selected from the group consisting of hydrogen peroxide, urea peroxide, sodium percarbonate. and PVP-$H_2O_2$; (iii) a gum health active selected from the group consisting of bachalin, polyphenols, triclosan, ethyl pyruvate, and guanidinoethyl disulfide; (iv) a nutritional ingredient selected from the group consisting of vitamins, minerals, amino acids, vitamin E. and folic acid; (v) a tartar control or anti-stain agent selected from the group consisting of phosphate salts, poinylphosphonic acid, and PVM/MA copolymer; (vi) a flavor or flavor ingredient selected from the group consisting of menthol, carvone, anethole, aldehydes, esters, alcohols, and oils of spearmint, peppermint, wintergreen, sassafras, dove, sage, eucalyptus, marjoram, cinnamon, lemon, lime, grapefruit, or orange; (vii) an occluding agent selected from the group consisting of bioactive glass and arginine salts; and combinations thereof.

5. The toothbrush of claim 1, wherein the reservoir is a replaceable cartridge.

6. The toothbrush of claim 1, which comprises a first section containing the handle, head, and channel, and a second section containing the reservoir, wherein the second section is releasably attached to the first section.

7. The toothbrush of claim 1 further comprising an outlet located on the first surface of the head, the capillary channel delivering the active agent from the reservoir to both the porous outlet on the second surface of the head by capillary action and to the outlet on the first surface of the head by capillary action.

8. The toothbrush of claim 1 wherein the capillary channel is a single tube of porous material.

9. The toothbrush of claim 1 wherein the reservoir includes a reticulated foam.

10. The toothbrush of claim 9 wherein the reticulated foam is an open cell polyurethane foam based on polyester.

11. The toothbrush of claim 9 wherein the reticulated foam averages 90 pores per inch.

12. The toothbrush of claim 1 further comprising:
   an outlet located on the first surface of the of the head, the capillary channel delivering the active agent from the reservoir to both the porous outlet on the second surface of the head by capillary action and the outlet on the first surface of the head by capillary action;
   wherein the reservoir includes a reticulated foam; and
   wherein the reticulated foam is an open cell polyurethane foam based on polyester averaging 90 pores per inch.

13. A toothbrush comprising:
   a handle;
   a head having a first surface containing at least one tooth cleaning element comprising bristles;
   a reservoir for storing an active agent;
   a porous outlet located on a second surface of the head opposite the first surface;
   a capillary channel that continuously delivers the active agent from the reservoir to the porous outlet by capillary action, wherein the capillary channel is made of a porous material;
   a soft tissue cleanser constructed of an elastomeric material positioned on the second suface of the head, the porous outlet incorporated into the soft tissue cleanser; and
   wherein the porous outlet comprises a non-woven pad or membrane through which the active agent can flow for application to an oral surface of a user.

14. A toothbrush comprising:

a handle;

a head having a first surface containing at least one tooth cleaning element comprising bristles;

a reservoir for storing an oral care material;

a porous outlet located on a second surface of the head opposite the first surface;

a capillary channel that delivers the oral care material from the reservoir to the porous outlet by capillary action, wherein the capillary channel is made of a capillary material and is in continuous fluid communication with the porous outlet; and a soft tissue cleanser constructed of an elastomeric material positioned on the second surface of the head, the porous outlet incorporated into the soft tissue cleanser.

15. The toothbrush of claim 14 wherein the oral care material is an active agent.

16. The toothbrush of claim 14 wherein the capillary material is selected from a group consisting of a fibrous material, a ceramic, a porous material, or combinations thereof.

17. A toothbrush comprising:

a handle;

a head having a first surface containing at least one tooth cleaning element comprising bristles;

a reservoir for storing an active agent;

an outlet located on a second surface of the head opposite the first surface;

a capillary channel that delivers the active agent from the reservoir to the outlet by capillary action, wherein the capillary channel is made of a capillary material and is in continuous fluid communication with the outlet; and a soft tissue cleanser constructed of an elastomeric material positioned on the second surface of the head, the outlet incorporated into the soft tissue cleanser.

\* \* \* \* \*